United States Patent
Kim et al.

(10) Patent No.: US 9,457,814 B2
(45) Date of Patent: Oct. 4, 2016

(54) APPARATUS AND METHOD FOR CONTROLLING DRIVING OF VEHICLE BASED ON DRIVER'S FATIGUE

(71) Applicant: HYUNDAI MOTOR COMPANY, Seoul (KR)

(72) Inventors: Seon Su Kim, Seongnam-Si (KR); Seung-Chang Park, Seoul (KR)

(73) Assignee: HYUNDAI MOTOR COMPANY, Seoul (KR)

(*) Notice: Subject to any disclaimer, the term of this patent is extended or adjusted under 35 U.S.C. 154(b) by 0 days.

(21) Appl. No.: 14/558,311

(22) Filed: Dec. 2, 2014

(65) Prior Publication Data
US 2015/0285653 A1    Oct. 8, 2015

(30) Foreign Application Priority Data
Apr. 4, 2014 (KR) ................ 10-2014-0040697

(51) Int. Cl.
| | |
|---|---|
| *B60W 40/04* | (2006.01) |
| *B60W 40/08* | (2012.01) |
| *A61B 5/145* | (2006.01) |
| *B60W 40/06* | (2012.01) |
| *A61B 5/0205* | (2006.01) |

(Continued)

(52) U.S. Cl.
CPC ............ *B60W 40/04* (2013.01); *A61B 5/0205* (2013.01); *A61B 5/18* (2013.01); *B60W 40/06* (2013.01); *B60W 40/08* (2013.01); *G01C 21/34* (2013.01); *A61B 5/021* (2013.01); *A61B 5/14532* (2013.01); *A61B 5/4005* (2013.01); *A61B 5/681* (2013.01); *A61B 5/6803* (2013.01); *A61B 5/6893* (2013.01); *B60W 2040/0827* (2013.01); *B60W 2540/26* (2013.01); *B60W 2550/12* (2013.01); *B60W 2550/14* (2013.01); *B60W 2550/20* (2013.01); *Y02T 10/84* (2013.01)

(58) Field of Classification Search
CPC ............ G01C 21/3484; A61B 5/021; A61B 5/14532; B60W 40/04; B60W 40/08
USPC ........................................................ 701/423
See application file for complete search history.

(56) References Cited

U.S. PATENT DOCUMENTS

| | | | |
|---|---|---|---|
| 2003/0043045 A1* | 3/2003 | Yasushi .................... | A61B 5/18 340/576 |
| 2011/0022298 A1 | 1/2011 | Kronberg | |

(Continued)

FOREIGN PATENT DOCUMENTS

| | | |
|---|---|---|
| JP | 4792865 B2 | 10/2011 |
| JP | 2013-069151 A | 4/2013 |

(Continued)

*Primary Examiner* — Fadey Jabr
*Assistant Examiner* — Yazan Soofi
(74) *Attorney, Agent, or Firm* — McDermott Will & Emery LLP

(57) ABSTRACT

An apparatus for controlling driving a vehicle based on driver's fatigue includes a first information collector to collect biological information of a driver, a second information collector collect road condition information, a route calculator configured to calculate a desired route from a current position of the vehicle to a destination, a fatigue index calculator to divide a route, and to calculate a fatigue index for each section, a predicted fatigue index calculator to calculate a predicted fatigue index corresponding to the desired route, and a function provider configured to calculate a compensation value according to the predicted fatigue index, and to calculate a final operation value.

4 Claims, 5 Drawing Sheets

(51) Int. Cl.
*A61B 5/18* (2006.01)
*G01C 21/34* (2006.01)
*A61B 5/021* (2006.01)
*A61B 5/00* (2006.01)

(56) References Cited

U.S. PATENT DOCUMENTS

2012/0150429 A1* 6/2012 Siotos ............... G01C 21/3617
 701/411
2014/0200800 A1* 7/2014 Vogel ............... G01C 21/3453
 701/400
2014/0276090 A1* 9/2014 Breed .................... A61B 5/18
 600/473
2014/0380264 A1* 12/2014 Misra .................... H04L 67/12
 717/100
2015/0045986 A1* 2/2015 Kan .................... B60W 40/08
 701/1

FOREIGN PATENT DOCUMENTS

| KR | 10-2013-0015739 A | 2/2013 |
| KR | 10-2013-0022298 A | 2/2013 |
| KR | 10-2013-0140874 A | 12/2013 |

* cited by examiner

APPARATUS AND METHOD FOR CONTROLLING DRIVING OF VEHICLE BASED ON DRIVER'S FATIGUE

CROSS-REFERENCE TO RELATED APPLICATION

This application claims priority to and the benefit of Korean Patent Application No. 10-2014-0040697 filed in the Korean Intellectual Property Office on Apr. 4, 2014, the entire contents of which are hereby incorporated by reference herein.

BACKGROUND OF THE DISCLOSURE (a) Field of the Disclosure

The present disclosure relates to an apparatus and a method for controlling driving of a vehicle based on driver's fatigue.

(b) Description of the Related Art

As driving time of a driver due to long distance driving and traffic congestion has increased, an occurrence rate of traffic accidents due to driver's fatigue has increased every year. The occurrence rate of traffic accidents due to driver's fatigue is higher than that of traffic accidents due to drinking and driving. Therefore, the driver needs to take a rest at a rest area for overcoming fatigue when the driver feels fatigue, but it is difficult for the driver to recognize his/her fatigue degree.

In recent years, an advanced driver assistance system (ADAS) that recognizes an accident risk in advance to prevent an accident or assist a driver's driving has been actively mounted on a vehicle. The advanced driver assistance system (ADAS) may include a lane departure warning system (LDWS), a lane keeping assist system (LKAS), a collision avoidance system (CAS), a driver drowsiness detection system, an auto cruise control (ACC) system, a parking assistance system (PAS), an autonomous emergency braking (AEB) system and the like. In the related art, the advanced driver assistance system performs a driver assistance function such as a lane departure warning function based on a preset operation value. In other words, the advanced driver assistance system has a problem in that the driver's fatigue is not reflected and the operation value is simply used. Accordingly, a method for providing an appropriate driver assistance function considering the driver's fatigue is required.

The above information disclosed in this Background section is only for enhancement of understanding of the background of the disclosure and therefore it may contain information that does not form the prior art that is already known in this country to a person of ordinary skill in the art.

SUMMARY OF THE DISCLOSURE

The present disclosure has been made in an effort to provide an apparatus and a method for controlling driving of a vehicle based on driver's fatigue having advantages of providing an appropriate driver assistance function to the driver by considering the driver's fatigue.

An apparatus for controlling driving of a vehicle based on driver's fatigue according to an exemplary embodiment of the present disclosure may include: a first information collector configured to collect biological information of a driver; a second information collector configured to collect road condition information including a road state and a road shape; a route calculator configured to calculate a desired route from a current position of the vehicle to a destination; a fatigue index calculator configured to divide a route on which the vehicle has traveled into a plurality of sections, and to calculate a fatigue index for each section using the biological information, and to correct the fatigue index using the road condition information; a predicted fatigue index calculator configured to calculate a predicted fatigue index corresponding to the desired route using the corrected fatigue index when the desired route is calculated; and a function provider configured to calculate a compensation value according to the predicted fatigue index, and to calculate a final operation value by applying the compensation value to a basic operation value, which is a reference for performing a driver assistance function, and to provide the driver assistance function based on the final operation value to the driver.

The biological information may include information regarding blood glucose, blood pressure, and a view of the driver and the predicted fatigue index may include a predicted blood glucose index, a predicted blood pressure index, and a predicted view index.

The function provider may calculate the compensation value (ΔT) from the equation $$\Delta T = \sum_{i=1}^{n} w_i \times x_i,$$

wherein $x_i$ represents the predicted fatigue index and $w_i$ represents a weight value corresponding to the driver assistance function and the predicted fatigue index.

The second information collector may collect environment information including information regarding fog, rain, snow, and an accident or not, and the function provider may correct the final operation value using the environment information.

A method for controlling driving of a vehicle based on driver's fatigue according to an exemplary embodiment of the present disclosure may include: collecting biological information of a driver and road condition information including a road state and a road shape dividing a route on which the vehicle has traveled into a plurality of sections and calculating a fatigue index for each section using the biological information; correcting the fatigue index using the road condition information; when a desired route is calculated, calculating a predicted fatigue index corresponding to the desired route using the corrected fatigue index and calculating a compensation value according to the predicted fatigue index; calculating a final operation value by applying the compensation value to a basic operation value which is a reference for performing a driver assistance function; and providing the driver assistance function according to the final operation value to the driver.

The biological information may include information regarding blood glucose, blood pressure, and a view of the driver and the predicted fatigue index may include a predicted blood glucose index, a predicted blood pressure index, and a predicted view index.

The compensation value (ΔT) may be calculated from the equation $$\Delta T = \sum_{i=1}^{n} w_i \times x_i,$$

wherein $x_i$ represents the predicted fatigue index and $w_i$ represents a weight value corresponding to the driver assistance function and the predicted fatigue index.

The method may further include collecting environment information including information regarding fog, rain, snow, and an accident or not; and correcting the final operation value using the environment information.

According to an exemplary embodiment of the present disclosure it is possible to provide an appropriate driver assistance function by considering the driver's fatigue. Therefore, safety of the driver can be made secure and traffic accidents can be prevented.

| Description of symbols | |
|---|---|
| 100: First information collector | 200: Second information collector |
| 310: Route calculator | 320: Fatigue index calculator |
| 330: Predicted fatigue index calculator | 340: Function provider |

DETAILED DESCRIPTION OF THE EMBODIMENTS

The present disclosure will be described more fully hereinafter with reference to the accompanying drawings, in which exemplary embodiments of the disclosure are shown.

Throughout the specification, unless explicitly described to the contrary, the word "comprise" and variations such as "comprises" or "comprising" will be understood to imply the inclusion of stated elements but not the exclusion of any other elements. In addition, the terms "-er", "or", and "module" described in the specification mean units for processing at least one function and operation, and can be implemented by hardware components or software components and combinations thereof.

Throughout the specification, a driver assistance function means an assistance function, which is related to convenience and safety of a driver, provided from an advanced driver assistance system (ADAS). For example, the driver assistance function may include a lane departure warning function of a lane departure warning system (LDWS), a lane keeping assist function of a lane keeping assist system (LKAS), a collision avoidance function of a collision avoidance system (CAS), an anti-drowsiness function of a driver drowsiness detection system, an auto cruise function of an auto cruise control (ACC) system, a parking assistance function of a parking assistance system (PAS), an emergency braking function of an autonomous emergency braking (AEB) system and the like.

Figure 1:
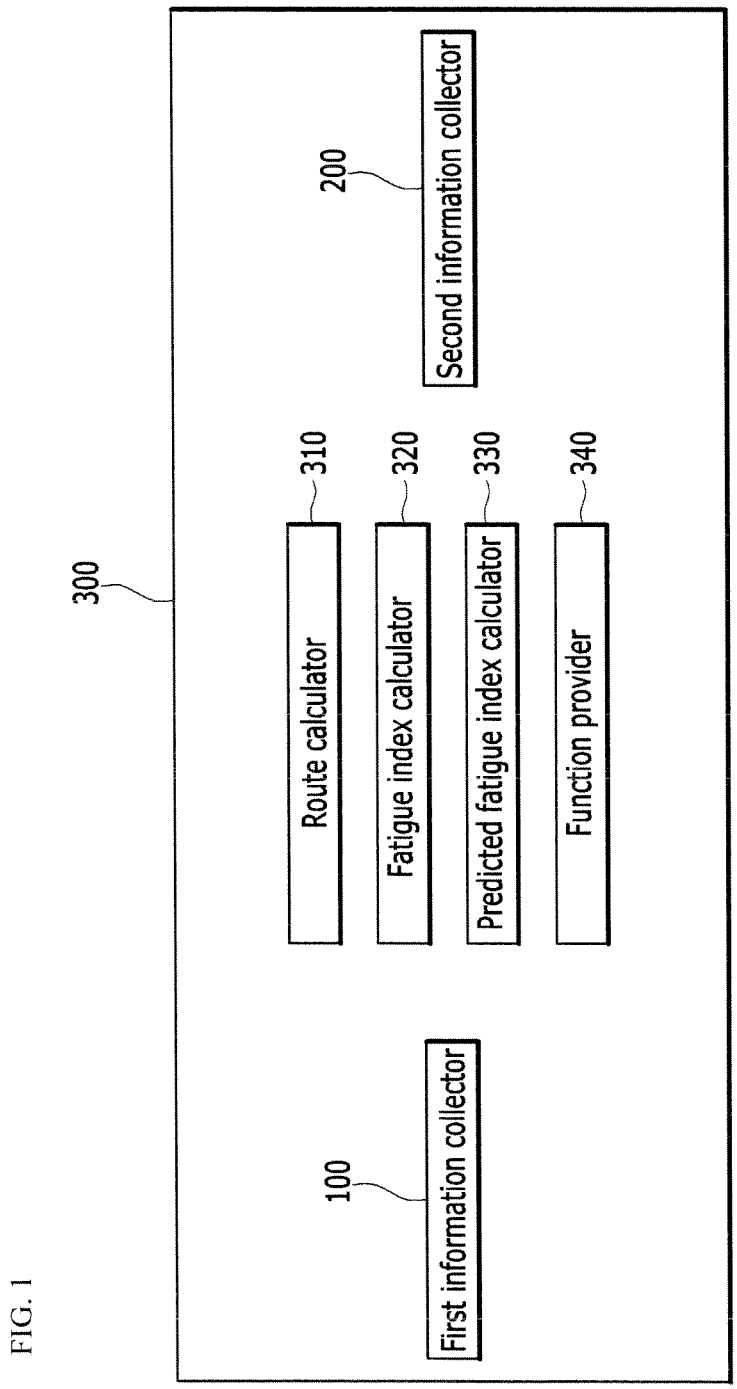
FIG. 1 is a block diagram of an apparatus for controlling driving of a vehicle based on driver's fatigue according to an exemplary embodiment of the present disclosure.

FIG. 1 is a block diagram of an apparatus for controlling driving a vehicle based on driver's fatigue according to an exemplary embodiment of the present disclosure.

As shown in FIG. 1, an apparatus 300 for controlling driving a vehicle according to an exemplary embodiment of the present disclosure may include a first information collector 100, a second information collector 200, a route calculator 310, a fatigue index calculator 320, a predicted fatigue index calculator 330, and a function provider 340.

The first information collector 100 collects biological information of a driver. The first information collector 100 may collect the biological information from a wearable device such as a watch-type device and glass-type device attached to a body part of the driver. The biological information may include information regarding blood glucose, blood pressure, and view of the driver, and the like. In addition, the first information collector 100 may collect destination information input from the driver.

The second information collector 200 collects road condition information including a road state and a road shape. The second information collector 200 may collect the road condition information from a remote server such as a telematics server. The road condition information may include the road state such as an icy road, a slippery road, a rough road, an unpaved road, an express way and a town road, and the road shape such as a flat road, a curve road and an inclined road. In addition, the second information collector 200 may include an environment information including information regarding fog, rain, snow, and an accident or not.

The route calculator 310 calculates a route from a current position of the vehicle to a destination. In detail, when the destination is input from the driver, the route calculator 310 sets the current position of the vehicle as a starting position and sets the destination to calculate a desired route of the vehicle.

Figure 3:
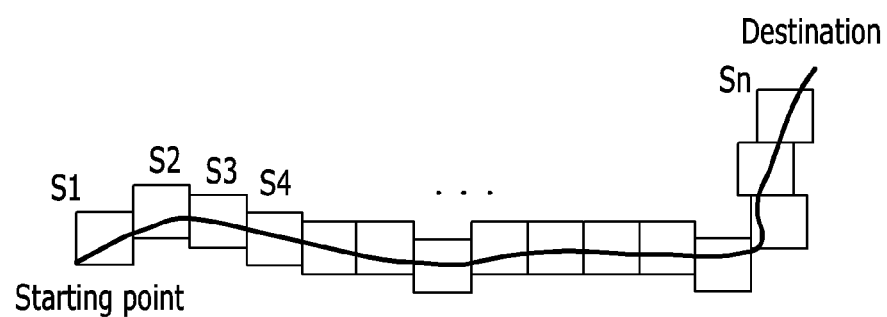
FIG. 3 is a drawing illustrating a plurality of sections according to an exemplary embodiment of the present disclosure.

The fatigue index calculator 320 divides a route on which the vehicle has traveled into a plurality of sections and calculates a fatigue index for each section using the biological information. The fatigue index may include a blood glucose index, a blood pressure index, a view index, and the like. For example, as shown in FIG. 3, the fatigue index calculator 320 may divide the route on which the vehicle has traveled according to a predetermined distance. Alternatively, the fatigue index calculator 320 may divide the route on which the vehicle has traveled into a plurality of sections according the road shape.

In addition, the fatigue index calculator 320 may correct the fatigue index using the road condition information including the road state and the road shape. For example, in the case that the road shape is an unpaved road, it is expected that driver's fatigue is increased. Therefore, the driver's fatigue can be precisely calculated by correcting the fatigue index using the road condition information.

The predicted fatigue index calculator 330 calculates a predicted fatigue index corresponding to the desired route using the corrected fatigue index when the route calculator 310 calculates a new route. The predicted fatigue index may include a predicted blood glucose index, a predicted blood pressure index, a predicted view index, and the like.

The function provider 340 provides the driver with a driver assistance function, which is related to convenience and safety of the driver, using the predicted fatigue index.

In detail, basic operation values, which are references for performing the driver assistance function, are set with respect to a lane departure warning function, a lane keeping assist function, a collision avoidance function, an anti-drowsiness function and the like, respectively. The basic operation value is set as a fixed value. The function provider 340 calculates a compensation value according to the predicted fatigue index. It also calculates a final operation value by applying the compensation value to the basic operation value, and provides the driver assistance function based on the final operation value to the driver. A process of calculating the final operation value will be described below with reference to FIG. 2.

Figure 2:
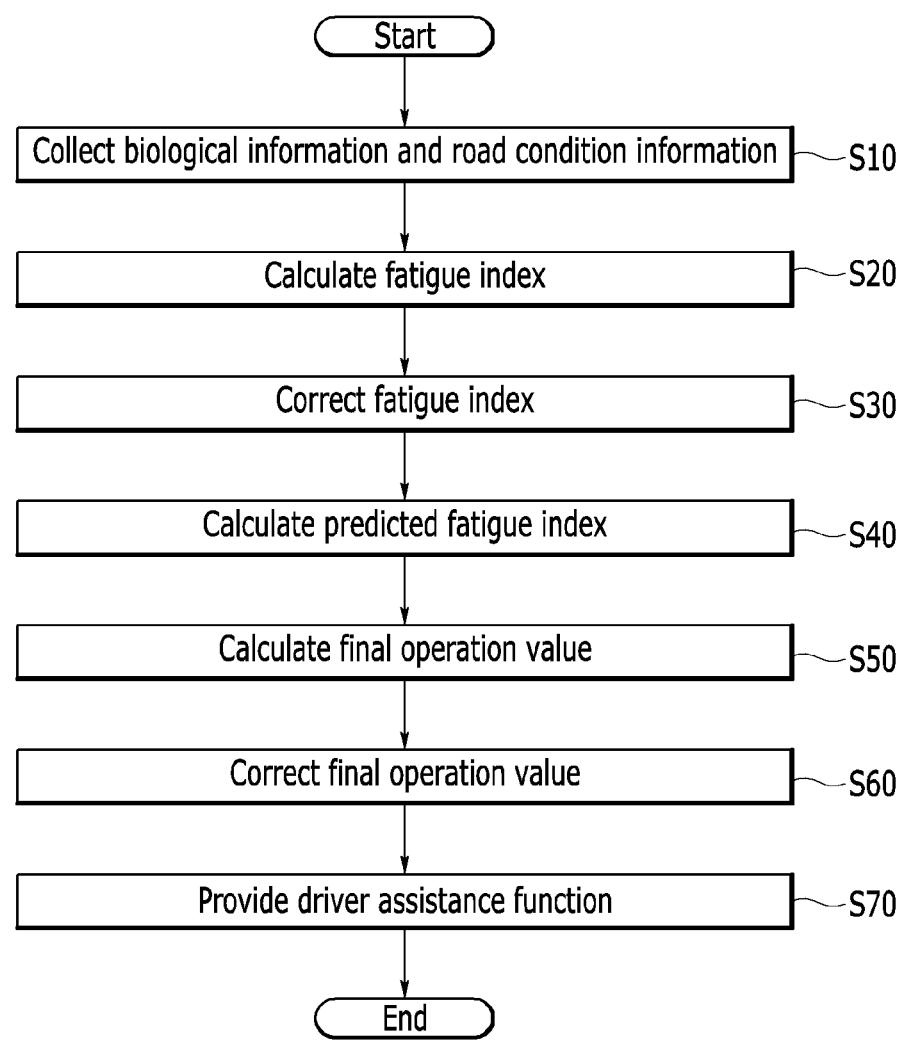
FIG. 2 is a flow chart of a method for controlling driving of a vehicle based on driver's fatigue according to an exemplary embodiment of the present disclosure.

FIG. 2 is a flow chart of a method for controlling driving of a vehicle based on driver's fatigue according to an exemplary embodiment of the present disclosure.

The first information collector 100 collects the biological information of the driver and the second information collector 200 collects the road condition information including the road state and the road shape at step S10. In this case, the second information collector 200 may collect the environment information including information regarding fog, rain, snow, an accident or not.

The fatigue index calculator 320 calculates the fatigue index using the biological information at step S20. In detail, the fatigue index calculator 320 may divide the route on which the vehicle has traveled into the plurality of sections and calculate the fatigue index for each section using the biological information.

The fatigue index calculator 320 corrects the fatigue index, which is calculated at step S20, using the road condition information including the road state and the road shape at step S30.

After that, when a new desired route is calculated by the route calculator 310, the predicted fatigue index calculator 330 calculates the predicted fatigue index corresponding to the desired route at step S40. The predicted fatigue index may include the predicted blood glucose index, the predicted blood pressure index, and the predicted view fatigue index. The predicted fatigue index calculator 330 may divide the desired route to a plurality of sections and calculate the predicted fatigue index for each section using the corrected fatigue index.

Figure 4:
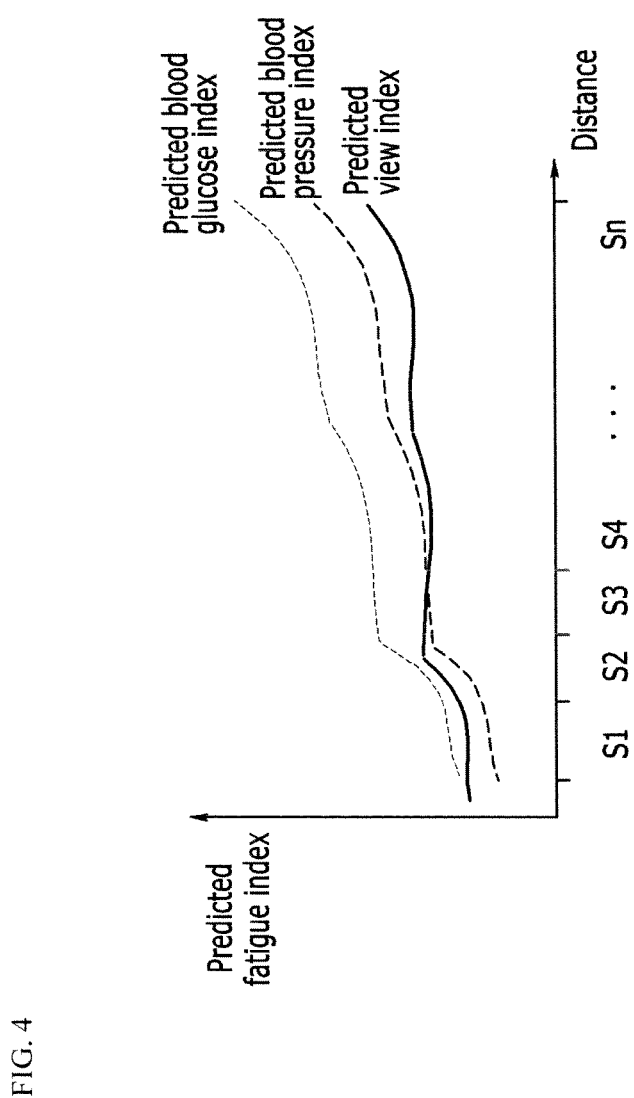
FIG. 4 is a graph illustrating a predicted fatigue index according to an exemplary embodiment of the present disclosure.

FIG. 4 is a graph illustrating a predicted fatigue index according to an exemplary embodiment of the present disclosure.

As shown in FIG. 4, as a distance between the current position of the vehicle and the destination decreases, the predicted blood glucose index, the predicted blood pressure index and the predicted view index may be increased. That is, driver's fatigue is increased as the distance between the current position of the vehicle and the destination decreases.

The function provider 340 calculates the final operation value of the driver assistance function for each section using the predicted fatigue index at step S50. The driver assistance function is related to convenience and safety of the driver.

Figure 5:
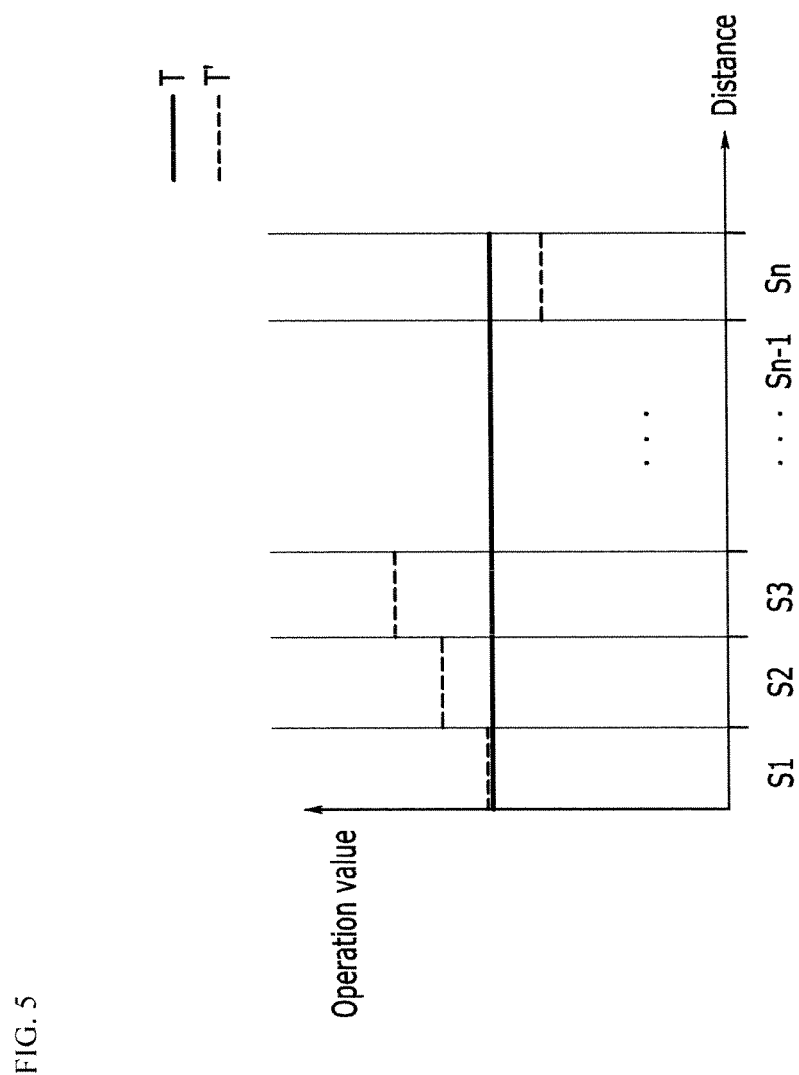
FIG. 5 is a graph illustrating a basic operation value and a final operation value according to an exemplary embodiment of the present disclosure.

FIG. 5 is a graph illustrating a basic operation value and a final operation value according to an exemplary embodiment of the present disclosure.

For example, as shown in FIG. 5, it can be verified that the basic operation value T and the final operation value T' for each section of the driver assistance function (e.g., lane keeping assist function) are calculated. In this case, the basic operation value T is set for the driver assistance function as a fixed value. The final operation value T' is a value that is changed with the predicted fatigue index.

The function provider 340 calculates the final operation value T' by applying a compensation value ΔT according to the predicted fatigue index to the basic operation value T by the below equation 1.

$$T' = T + \Delta T \quad \text{(Equation 1)}$$

The function provider 340 calculates the compensation value T by the below equation 2.

$$\Delta T = \sum_{i=1}^{n} w_i \times x_i, \quad \text{(Equation 2)}$$

Herein, n is a natural number and indicates the number of the predicted fatigue index. $x_i$ indicates the predicted fatigue index and $w_i$ indicates a weight value corresponding to the driver assistance function and the predicted fatigue index. In addition, the sum of the n weight values is 1.

For example, the driver assistance function provided by the function provider 340, the predicted fatigue index $x_i$, and the weight value $w_i$ are shown in Table 1.

TABLE 1

|  | Lane keeping assist function (LKAS) | Lane departure warning function (LDWS) | Collision avoidance function (CAS) | ... |
|---|---|---|---|---|
| Predicted blood glucose index ($x_1$) | 10% ($w_1$) | 10% ($w_1$) | 15% ($w_1$) | ... |
| Predicted blood pressure index ($x_2$) | 10% ($w_2$) | 5% ($w_2$) | 5% ($w_2$) | ... |
| Predicted view index ($x_3$) | 20% ($w_3$) | 35% ($w_3$) | 20% ($w_3$) | ... |
| ($x_4$) | 30% ($w_4$) | 35% ($w_4$) | 20% ($w_4$) | ... |
| ... | ... | ... | ... | ... |

For example, a driving mode provided by the function provider 340, the predicted fatigue index $x_i$, and the weight value $w_i$ are shown in Table 2.

TABLE 2

|  | Normal mode | Comfort mode | Sport mode | 4WD/2WD mode | Eco mode | ... |
|---|---|---|---|---|---|---|
| Predicted blood glucose index ($x_1$) | 20% ($w_1$) | 5% ($w_1$) | 20% ($w_1$) | 5% ($w_1$) | 5% ($w_1$) | ... |
| Predicted blood pressure index ($x_2$) | 20% ($w_2$) | 5% ($w_2$) | 20% ($w_2$) | 5% ($w_2$) | 5% ($w_2$) | ... |
| Predicted view index ($x_3$) | 20% ($w_3$) | 20% ($w_3$) | 30% ($w_3$) | 10% ($w_3$) | 20% ($w_3$) | ... |
| ($x_4$) | 10% ($w_4$) | 20% ($w_4$) | 10% ($w_4$) | 10% ($w_4$) | 20% ($w_4$) | ... |
| ... | ... | ... | ... | ... | ... | ... |

The function provider 340 corrects the final operation value T' using the environment information including information regarding fog, rain, snow, and an accident or not at step S60.

The function provider 340 may correct the final operation value T' using a weight value corresponding to the environment information as shown in Table 3.

TABLE 3

| Environment information | Weight value |
|---|---|
| Fog or not | −1% |
| Rain or not | −3% |
| Snow or not | −10% |
| Accident or not | −11% |

The function provider 340 provides the driver assistance function or the driving mode to the driver based on the final operation value T' at step S70.

As described above, according to an exemplary embodiment of the present disclosure, it is possible to provide the appropriate driver assistance function or driving mode to the driver using the predicted fatigue index for each section of the desired route. Driver assistance function and driving mode suitable to a current state of the driver may be provided by controlling sensitivity of the driver assistance function and driving mode according to the predicted fatigue index.

While this disclosure has been described in connection with what is presently considered to be practical exemplary embodiments, it is to be understood that the disclosure is not limited to the disclosed embodiments, but, on the contrary, is intended to cover various modifications and equivalent arrangements included within the spirit and scope of the appended claims.

What is claimed is:

1. An apparatus for controlling driving of a vehicle based on driver's fatigue, comprising:
   a first information collector configured to collect biological information of a driver;
   a second information collector configured to collect road condition information including a road state and a road shape;
   a route calculator configured to calculate a desired route from a current position of the vehicle to a destination;
   a fatigue index calculator configured to divide a route on which the vehicle has traveled into a plurality of sections, and to calculate a fatigue index for each section using the biological information, and to correct the fatigue index using the road condition information;
   a predicted fatigue index calculator configured to calculate a predicted fatigue index corresponding to the desired route using the corrected fatigue index when the desired route is calculated; and
   a function provider configured to calculate a compensation value according to the predicted fatigue index, and to calculate a final operation value by applying the compensation value to a basic operation value, which is a reference for performing a driver assistance function, and to perform the driver assistance function based on the final operation value to the driver,
   wherein the biological information includes information regarding blood glucose, blood pressure, and a view of the driver, and the predicted fatigue index includes a predicted blood glucose index, a predicted blood pressure index, and a predicted view index, and
   wherein the function provider calculates the compensation value (ΔT) from the equation $$\Delta T = \sum_{i=1}^{n} w_i \times x_i,$$

wherein $x_i$ represents the predicted fatigue index and $w_i$ represents a weight value corresponding to the driver assistance function and the predicted fatigue index, and a sum of n weight values is 1.

2. The apparatus of claim 1, wherein the second information collector collects environment information including information regarding fog, rain, snow, and an accident or not, and the function provider corrects the final operation value using the environment information.

3. A method for controlling driving of a vehicle based on driver's fatigue, comprising:
   collecting biological information of a driver and road condition information including a road state and a road shape;
   dividing a route on which the vehicle has traveled into a plurality of sections and calculating a fatigue index for each section using the biological information;
   correcting the fatigue index using the road condition information;
   when a desired route is calculated, calculating a predicted fatigue index corresponding to the desired route using the corrected fatigue index and calculating a compensation value according to the predicted fatigue index;
   calculating a final operation value by applying the compensation value to a basic operation value which is a reference for performing a driver assistance function; and
   performing the driver assistance function according to the final operation value to the driver,
   wherein the biological information includes information regarding blood glucose, blood pressure, and a view of the driver, and the predicted fatigue index includes a predicted blood glucose index, a predicted blood pressure index, and a predicted view index, and
   wherein the compensation value (ΔT) is calculated from the equation $$\Delta T = \sum_{i=1}^{n} w_i \times x_i,$$

wherein $x_i$ represents the predicted fatigue index and $w_i$ represents a weight value corresponding to the driver assistance function and the predicted fatigue index, and a sum of n weight values is 1.

4. The method of claim 3, further comprising:
   collecting environment information including information regarding fog, rain, snow, and an accident or not; and
   correcting the final operation value using the environment information.

* * * * *